United States Patent [19]

Poler

[11] 4,326,306
[45] Apr. 27, 1982

[54] INTRAOCULAR LENS AND MANIPULATING TOOL THEREFOR

[75] Inventor: Stanley Poler, New York, N.Y.

[73] Assignee: Lynell Medical Technology, Inc., New York, N.Y.

[21] Appl. No.: 216,787

[22] Filed: Dec. 16, 1980

[51] Int. Cl.³ .......................... A61F 1/16; A61F 1/24
[52] U.S. Cl. ..................... 3/13; 128/303 R; 206/5.1; 206/205; 206/210
[58] Field of Search .................. 3/13; 128/303 R; 206/5.1, 205, 210

[56] References Cited

U.S. PATENT DOCUMENTS

| | | | |
|---|---|---|---|
| 4,122,556 | 10/1978 | Poler | 3/13 |
| 4,136,406 | 1/1979 | Norris | 3/13 |
| 4,159,546 | 7/1979 | Shearing | 3/13 |
| 4,242,760 | 1/1981 | Rainin | 3/13 |

FOREIGN PATENT DOCUMENTS 2717706 10/1978 Fed. Rep. of Germany ............ 3/13

Primary Examiner—Ronald L. Frinks
Attorney, Agent, or Firm—Hopgood, Calimafde, Kalil, Blaustein & Judlowe

[57] ABSTRACT

The invention contemplates improved techniques for making lens implants for use in ophthalmological surgery, the lens being a replacement for a cataract-clouded natural lens. The lens of the invention is particularly adapted for posterior-chamber implantation, with position stability derived from the inner wall of the natural-lens sac (from which cataracted material has been removed). A manipulative tool in combination with the lens assembly (1) provides safe stabilizing support during storage and transit prior to the surgeon's access for operative use, and (2) is configurated to facilitate operative placement of compliant retaining feet within the sac, permitting posterior-chamber positioning of the lens prior to tool removal.

14 Claims, 9 Drawing Figures

INTRAOCULAR LENS AND MANIPULATING TOOL THEREFOR

BACKGROUND OF THE INVENTION

The invention relates to structures for making an improved lens implant, as a replacement for a cataract-clouded or otherwise diseased natural lens. The invention represents improvement and modification with respect to structures described in my U.S. Pat. No. 4,122,556 and in my copending application Ser. No. 057,323, filed July 13, 1979, now U.S. Pat. No. 4,249,271. Reference is therefore made to said patent and application for greater background detail.

In said copending application, certain structures and techniques are described for the posterior-chamber implantation of a lens, with foot-stabilized haptic reference to the inner wall of the sac from which cataracted material has been removed. The techniques generally involved use of a releasable filamentary tie of the stabilizing feet after their insertion into the volume of the sac. But such techniques have their limitations, requiring the preliminary step of creating the tie while transiently deforming the feet, and no additional function is provided by the filamentary tie.

BRIEF STATEMENT OF THE INVENTION

It is an object of the invention to provide improved intraocular-lens mounting structure and means for operatively manipulating the same.

It is a specific object to meet the above object for the case of a posterior-chamber implantation wherein stabilizing reference is derived from the inner wall of a natural-lens sac from which cataracted material has been removed.

Another specific object is to provide improved manipulative-tool means for achieving the above objects.

A further specific object is to provide such a tool which can be factory preassembled to a lens-and-mount assembly, and which is selectively useful (1) to provide essentially flat and stress-free stabilizing support of the lens assembly during storage and/or shipment, and (2) to efficiently cluster and hold positioning haptic feet for easy release within the sac, upon simple withdrawal of the tool.

The invention achieves the foregoing objects and other features using a manipulative tool in combination with particular varieties of lens-and-mount assemblies. In a first assembled relation of the tool to the lens-and-mount assembly, the latter is centrally positioned and stabilized within a hook-shaped end of the tool, all haptic elements being substantially flat and stress-free, in the same general plane as the hook-shaped end. Without disturbing the assembly of the lens, haptic and tool, and merely by shifting the location of haptic assembly to the tool, the stabilizing feet of the haptic are clustered and positioned for safe and accurate placement within the sac, in readiness for their instant release to develop sac-wall engagement, upon tool withdrawal.

DETAILED DESCRIPTION

The invention will be illustratively described in conjunction with the accompanying drawings, in which.

Figure 1:
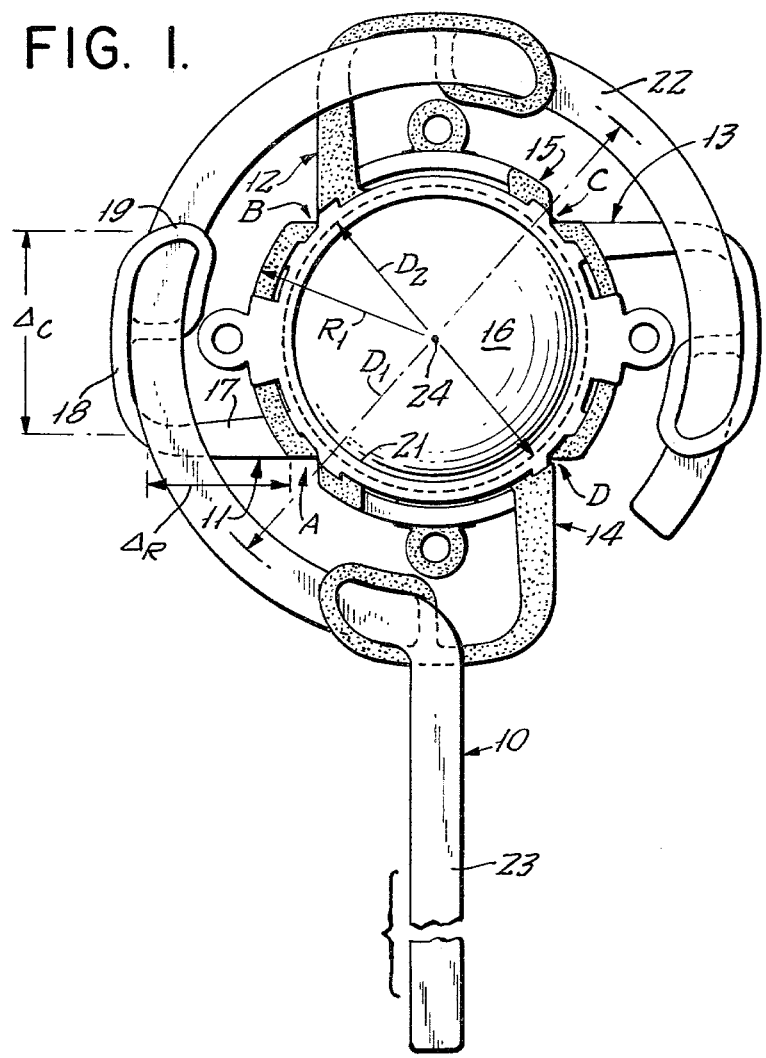
FIG. 1 is a plan view, on an enlarged scale, showing a tool of the invention in combination with an implant lens and haptic structure, for a first relationship wherein the haptic structure is substantially flat and stress-free, and yet the lens is safely positioned for storage and/or transport.

In FIG. 1, the invention is shown involving use of a tool 10 in a first assembled relation to stabilizing feet 11-12-13-14 of haptic body structure 15 which circumferentially engages and retains an intraocular lens 16, which is preferably of optically finished glass. The feet 11-12-13-14 are shown to be of the so-called open-loop variety, comprising a radially offsetting leg portion 17 and an outer circumferentially extending arm portion 18 which terminates at a loop 19 of such internally open span and area as to readily accept threaded assembly of the tool 10 thereto. Feet 11-12-13-14 are integral formations with body structure 15, which is preferably of thin flexible plastic sheet material that is inert to body fluids.

Figure 2:
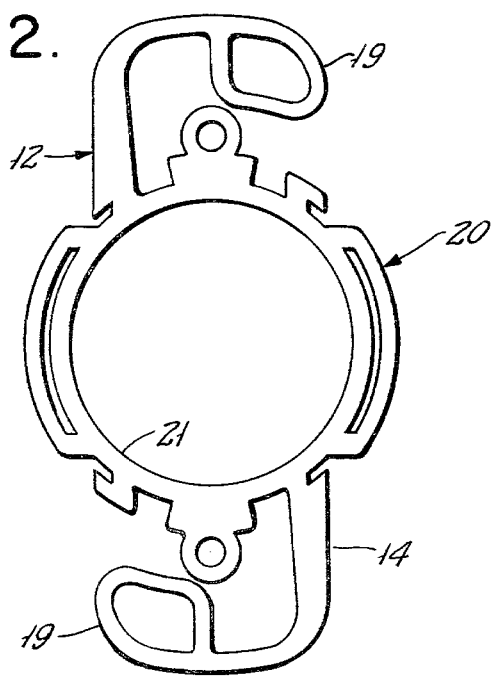
FIG. 2 is a plan view of one of the mounting-element or haptic components of FIG. 1.

In the form shown, the mounting assembly for the lens 16 comprises two like haptic blanks, such as the blank 20 of FIG. 2, assembled to each other via hook-and-slot engagements outside the periphery of lens 16, and having circular inner edges 21 which are of lesser diameter than the rim of lens 16 and which overlap opposite sides of the rim for lens retention. Such hook-and-slot relationships are discussed in detail in said pending application and therefore require no present elaboration.

The tool 10 is shown also to be formed from flat stock, being preferably of compliant sheet plastic material inert to body fluids. The material of tool 10, although compliantly bendable, is nevertheless more stiffly compliant than the heptic material, the tool stiffness being suitably in the range of 5 to 10 times the haptic stiffness. Tool 10 consists of a hook-shaped end 22 integrally connected to a shank end 23, the shank end 23 extending radially outward of the inner end of the hook shape 22. The sectional area or width of tool 10 material is substantially constant, being suitably 0.04-inch wide, 0.004-inch thick, and of the same material (polyimide) as the haptic structure. The mean diameter $D_1$ of the hook shape 22 should coincide with the diameter of the geometrical circle which contains the radial midpoints of all loops 19, the latter being taken in reference to the central optical axis 24. This relationship will be seen to assure an unstressed yet centrally stabilizing condition of the haptic structure when assembled, as shown, to the hook-shaped end 22. Preferably, the openings defined within loops 19 are circumferentially elongate, as shown, to further assure the unstressed nature of the haptic when supported in this flat condition. The hook-shaped end 22 is effectively of an arcuate extent exceeding $3\pi/2$ radians about the center of the lens-and-mount assembly when assembled to the feet loops 19.

It is important to note, for purposes of the invention, that each of the flexible feet 11-12-13-14 places its associated loop 19 at such effective radial offset $\Delta_R$ (with respect to the lens-rim diameter $D_2$) and at such effective circumferential offset $\Delta_C$ as to exceed the lens radius $$\left(\frac{D_2}{2}\right),$$

and preferably to exceed the lens-retaining body radius $R_1$ when the offset arms 17-18 are flexibly distended (i.e., $\Delta_R + \Delta_C > R_1$). Use is made of this fact in the further manipulation of described parts, as will appear from FIGS. 3 and 4.

Figure 3:
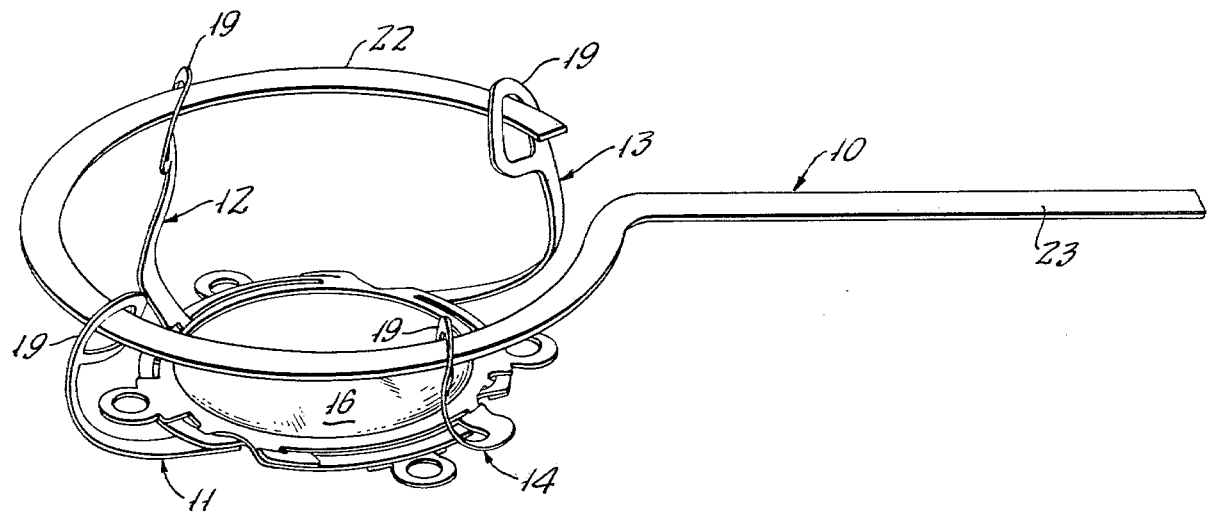
FIG. 3 is a perspective view of the tool, lens and haptic structure of FIG. 1, for a first changed relation of parts, preparatory to operative use.
Figure 4:
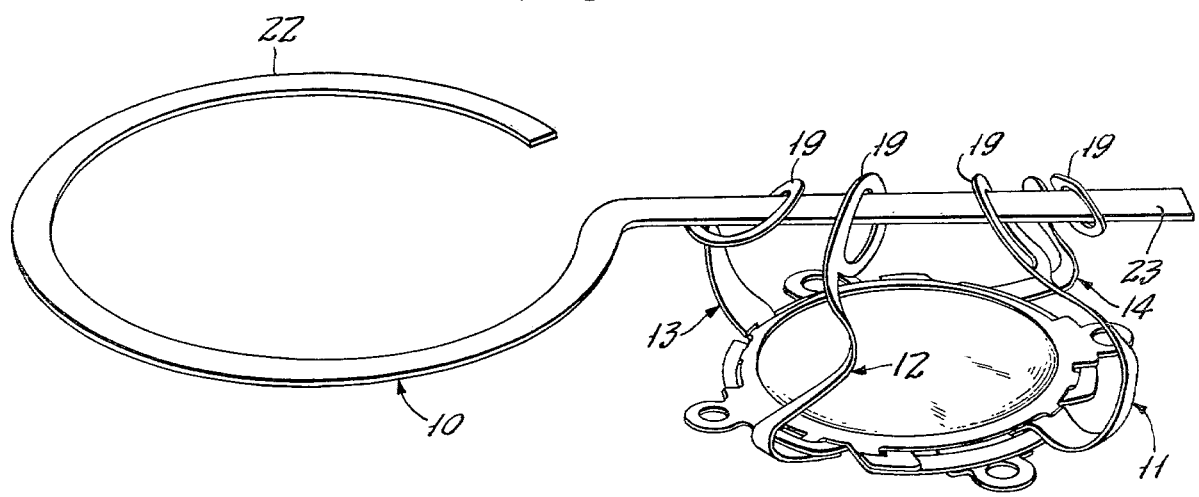
FIG. 4 is a view similar to FIG. 3, for a second changed relation of parts, preparatory to operative use.
Figure 5:
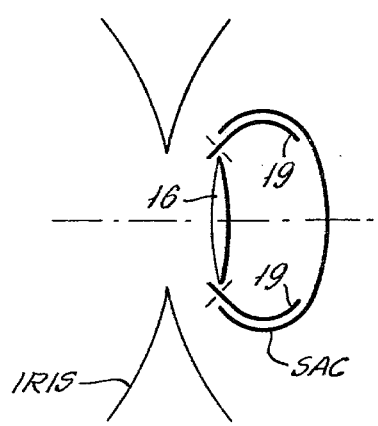
FIG. 5 is a simplified diagram to show implantation relationships within the posterior chamber of an eye following use of the tool of FIGS. 1, 3 and 4.

In FIG. 3, all of the loops 19 have been elevated by lifting tool 10, to allow lens 16 and the lens-retaining annular body 15 of the haptic to suspend compliantly via feet 11-12-13-14. The action has been to distend all offset arms 17-18, to establish a suspension offset of lens 16 below the hook-shaped end 22, to at least the extent $R_1$. With this suspension offset, it becomes readily possible to advance all loops 19 toward and onto the shank end 23 of the tool, as shown in FIG. 4, and it will be understood that with simple spatula or tweezer manipulation, all loops 19 may be closely arrayed in a cluster, at the outer end of shank 23, for collective placement within an excavated natural-lens sac.

An implant operation proceeds by positioning the loop (19) cluster within the sac while manipulating lens 16 via its retaining haptic body 15 through a dilated iris and into desired posterior-chamber placement, the shank 23 being removed, with spatula retention of the nearest loop 19 (for foot 13), if necessary, to release all feet 11-12-13-14 for resilient conformation to the local inner-wall contour of the sac.

Figure 6:
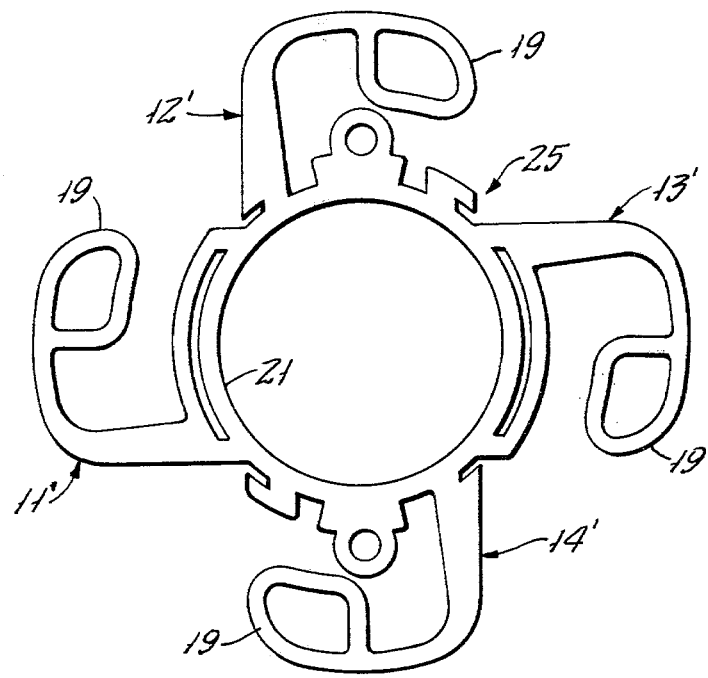
FIG. 6 is a view similar to FIG. 2, to show a modification.

FIG. 6 illustrates a modification wherein a single blank 25 is formed with all four haptic feet 11'-12'-13'-14', corresponding to feet 11-12-13-14 of FIG. 1, and having the same rim (21) diameter as for each of the two-foot haptic pieces (FIG. 2) used in the FIG. 1 assembly. The blank 25 is used in combination with an annular retaining ring having none of the haptic feet but having an inner rim which matches rim 21 for lens-retaining purposes. Such annular ring is assembled to blank 25 via hook-and-slot engagements similar to those of FIG. 1 and as more fully described in my said copending application Ser. No. 057,323, and therefore need not now be further described.

Figure 7:
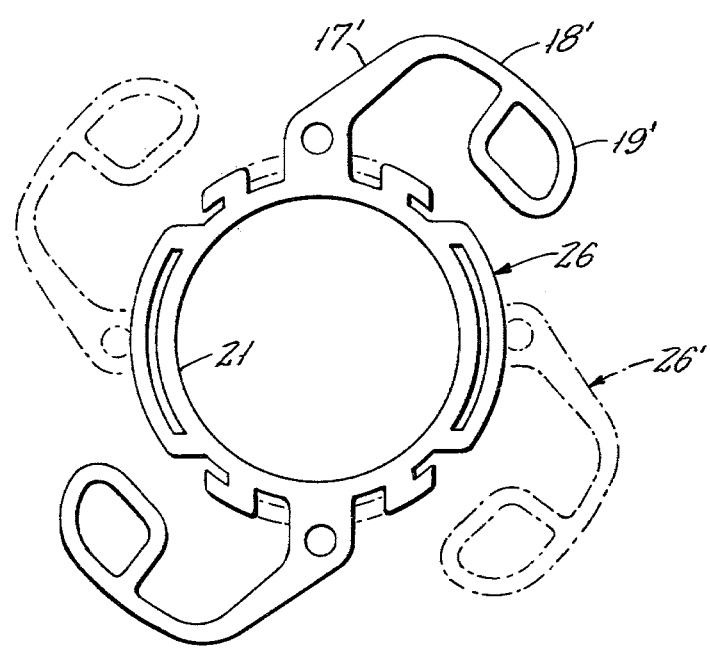

FIG. 7 illustrates a modified foot structure integrally formed into a haptic blank 26 which is otherwise similar to that of the blank 20 (FIG. 2). Each such foot is characterized by an outer circumferentially arcuate arm portion 18' integrally connected to the central body annulus by a leg portion 17' which is angularly slanted from radial, in the direction in which arm portion 18' extends. Again, a tool-engageable loop 19' characterizes the outer cantilevered end of each foot. Two such blanks 26 (26'), oriented at 90° interlacing of feet, are hook-and-slot engaged to each other to retain a lens 16, as will be understood from the description of FIG. 1. Alternatively, the phantom showing of such interlaced feet for blank 26' will be understood to define (with those of blank 26) the full contour of a four-leg blank as described in connection with FIG. 6. In either alternative, the slant leg (17') nature of haptic feet in FIG. 7 enables greater leg length and, therefore, a more gently compliant conformance to local sac contour, once released from tool 10 for stabilized positioning of the implanted lens 16.

Figure 8:
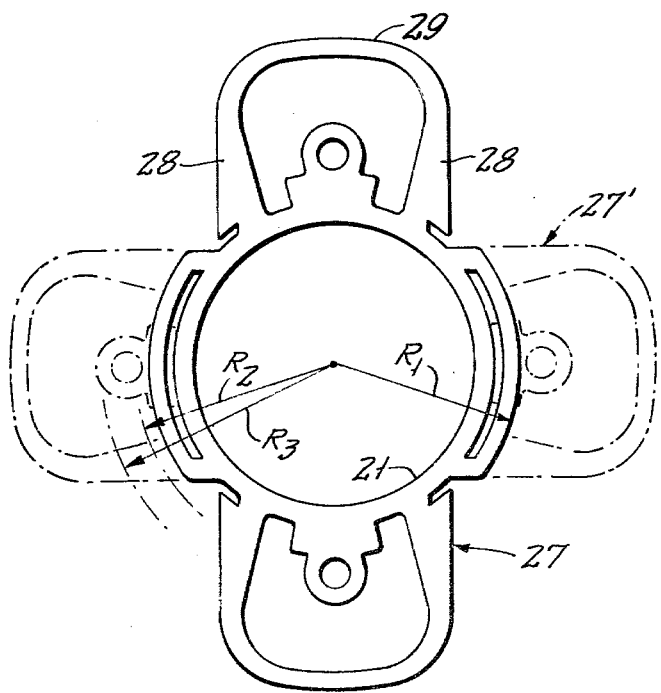
FIGS. 7 and 8 are views similar to FIG. 2, to show further modifications.

FIG. 8 illustrates a further haptic-blank modification, wherein the blank 27 has looped feet and therefore does not involve the cantilever-type support of the forms of FIGS. 1, 6 and 7. More specifically, each such looped foot comprises two spaced radially extending leg portions 28 which are integrally connected by an arcuate bridge portion 29 at their outer ends and which are integrally connected at the inner ends to the annular body of the blank. Again, as in FIG. 7, additional phantom showing (27') of such further feet at 90° interlace with those of blank 27 will be understood to suggest retention of a lens 16 either (a) by means of two hook-and-slot engaged separate blanks 27-27' or (b) by means of a single four-leg configuration (in the manner of FIG. 6) in conjunction with an annular ring having no foot formations. In the case of looped-foot haptics as in FIG. 8, it will be understood that the hook end 22 of tool 10 is initially assembled via the loops of successive feet and that the haptic-and-lens assembly is manuevered to the shank 23 of tool 10 in the manner described in connection with FIGS. 3 and 4. A preference is noted that, for use with FIG. 8 haptics, the hooked end 22 of tool 10 be formed with inner radius $R_2$ to more closely clear the annular body radius $R_1$ and with outer radius $R_3$ to more substantially clear the bridge portions 29, all as suggested by legend in FIG. 8, thus permitting an initially drooped suspension of the lens 16 when at the FIG. 3 stage of tool manipulation of the assembled lens and haptic, as will be understood.

For packaging and shipment purposes, a tool 10 in flat assembled relation to its associated lens 16 and haptic structure (e.g. as in FIG. 1) may very suitably be accommodated by the packaging means of my copending application Ser. No. 094,912, filed Nov. 16, 1979, now U.S. Pat. No. 4,257,521, with but small modification. Reference is therefore made to said application for full discussion, and only abbreviated discussion is needed here.

Figure 9:
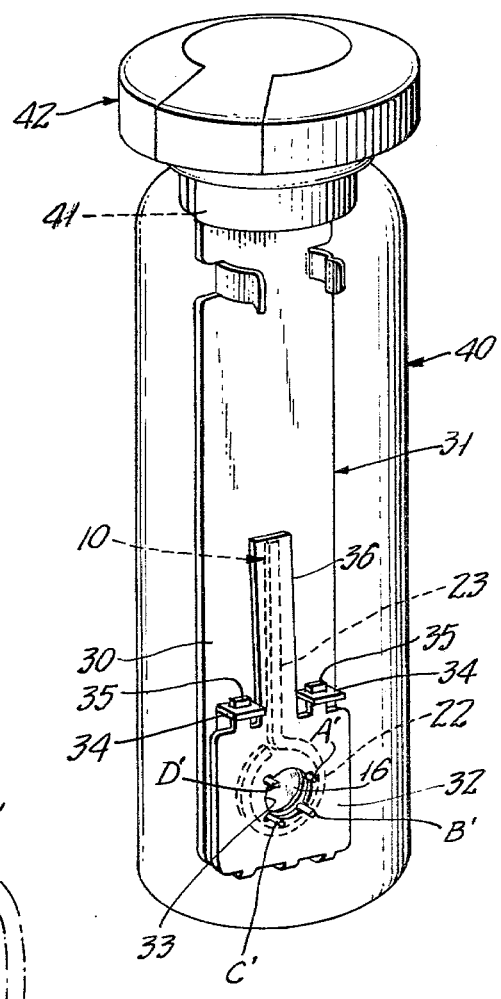
FIG. 9 is a simplified view in perspective, to show packaged use of the invention.

Briefly, each of four 90°-spaced locating notches A-B-C-D of the lens-and-haptic assembly receive similarly spaced upstanding locating pin-like lugs A'-B'-C'-D', which are bent up from the base panel 30 of an elongate mount 31, formed from a one piece blank of thin stainless-steel sheet. At its lower end, panel 30 is integrally formed for compliant folded connection to a closure flap or panel 32, designed to retain tool 10 and its assembled elements between panels 30-32; thus retained, lens 16 is viewable through an opening 33 in panel 32 which will be understood to register with a corresponding opening in panel 30. Two laterally spaced upstanding lugs 34 have latch formations such as slot openings for snap-action engagement with and retention of corresponding latch projections 35 on the adjacent edge portions of flap 30. The lateral space between lugs 34 is sufficient to accommodate the shank end 23 of tool 10 and to accommodate the central upwardly extending tongue-like end 36 of flap 32. When in the latched position shown in FIG. 9, tongue 36 retains tool shank 23 against panel 30. When latches at 34-35 are released, flap 32 springs to a sufficiently acute angle to permit outward bending via tongue 36, thus exposing the tool shank for grasping removal (from A-B-C-D location), and manipulation, as previously described.

As in said application Ser. No. 094,912, panel 30 may further include an elongate aperture 37 to receive the bent end of a hypodermic-needle tool 38, spring-retained by further lug formations 39 of panel 30. The described tools 38-10 and the lens-and-haptic assembly, retained as described, is packaged within a glass vial 40, closed and sealed by an elastomeric stopper 41 and protective tear-off cap 42.

The described haptic structures and manipulative tool will be seen to meet all stated objects. Operative procedure is greatly facilitated by having tool 10 preassembled to the lens-and-haptic assembly, the only pre-implantation step being to maneuver the haptic-foot ends 19 from the hook region 22 to the shank region 23 of tool 10. The vial 40 and its associated mounting components are fully autoclavable along with the retained tool 10 and the lens-and-haptic assembly, providing utmost readiness for use.

While the invention has been described in detail for preferred embodiments, it will be understood that modification may be made without departure from the scope of the invention.

What is claimed is:

1. In combination, a manipulable tool for substantially flat shipping support for an intraocular lens-and-mount assembly wherein a lens having a circular periphery is circumferentially retained, the mount of said assembly including flexibly compliant apertured iris-stabilizing feet projecting radially outward of plural angularly spaced regions of the lens-retaining circumference of said assembly, said tool comprising a generally hook-shaped end and a shank end integrally connected and with substantially constant cross-section, the apertures of said feet being of open section to clear said substantially constant cross-section and being assembled in circumferential succession to said tool, the span of said hook-shaped end being such as to accommodate assembly to all said feet at angularly spaced locations with the lens of said mount assembly centrally positioned within said hook-shaped end and with said feet in essentially flat unstressed condition, for generally central stabilized retention of the lens during storage and/or shipment, the effective compliantly achievable length of said feet exceeding the radius of circumferential retention of the lens, whereby upon lifting said tool, said lens and the circumferentially retaining portion of said mount become compliantly suspended beneath said hook-shaped end and said feet may be manipulated into clustered relation at the shank end of said tool, for cluster-grouped insertion of said feet into an excavated lens sac in the course of posterior-chamber implantation of the lens, so that said tool may be withdrawn to release said feet within the sac for compliant stabilizing conformance with sac inner-wall contouring to retain the lens anterior to said feet and in the posterior chamber.

2. The combination of claim 1, in which the hook-shaped end of said tool is along a circular arc of diameter which substantially conforms to the diameter of the circular locus of foot apertures when said mount is in flat condition.

3. The combination of claim 1, in which said hook-shaped end and said shank end are in substantially the same plane.

4. The combination of claim 1, in which said tool is of flat stock and said ends are of substantially constant width and thickness.

5. The combination of claim 1, in which said tool is of completely bendable material inert to body fluids, the stiffness of such compliant bendability exceeding the stiffness of the flexible compliance of said feet.

6. The combination of claim 1, in which said mount is of plastic sheet material and includes an annular lens-retaining body portion with which said feet are integrally formed, each of said feet being of open-loop configuration in which the foot aperture is both radially and angularly offset from the location of body connection.

7. The combination of claim 6, in which each said foot is characterized by a body-connected radially outward leg and an outer circumferentially extending end.

8. The combination of claim 7, in which an intermediate leg connects said radial leg to said circumferentially extending end, said intermediate leg being slope-characterized with both radially and angularly offsetting components.

9. The combination of claim 1, in which said mount is of plastic sheet material and includes an annular lens-retaining body portion with which said feet are integrally formed, each of said feet being of closed-loop configuration in which the foot aperture is defined by the closed loop.

10. The combination of claim 9, in which each closed-loop comprises two angularly spaced substantially parallel body-connected radially outward legs and an outer circumferentially extending end integrally connected to the ends of said legs.

11. The combination of claim 1, in which the number of feet is four and said hook-shaped end is effectively of arcuate extent exceeding $3\pi/2$ radians about the center of said assembly, when assembled to said hook-shaped end.

12. The combination of claim 1, in which said mount is of plastic sheet material and includes an annular lens-retaining body portion with which said feet are integrally formed, said body portion comprising a plurality of plastic-sheet elements assembled to each other via engagements outside the periphery of the lens and defining circular inner lens-retaining edges in radial overlap with the respective axial sides of the periphery of the lens.

13. The combination of claim 12, in which said feet are all integrally formed with the same single one of said sheet elements.

14. The combination of claim 12, in which said body portion comprises two sheet elements which are essentially duplicates of each other, each sheet element having two diametrically opposed feet, and said sheet elements being assembled to each other and to the lens with their respective diametrically opposed feet in angular interlace.

* * * * *

UNITED STATES PATENT AND TRADEMARK OFFICE
CERTIFICATE OF CORRECTION

PATENT NO. : 4,326,306
DATED : April 27, 1982
INVENTOR(S) : Stanley Poler

It is certified that error appears in the above—identified patent and that said Letters Patent is hereby corrected as shown below:

Column 6, line 10:

Claim 5    Change "completely" to -- compliantly --.

Signed and Sealed this

Sixth Day of July 1982

[SEAL]

Attest:

GERALD J. MOSSINGHOFF

Attesting Officer    Commissioner of Patents and Trademarks